(12) United States Patent
Klee et al.

(10) Patent No.: US 9,289,360 B2
(45) Date of Patent: Mar. 22, 2016

(54) DENTAL COMPOSITION

(71) Applicant: DENTSPLY International Inc., York, PA (US)

(72) Inventors: Joachim E. Klee, Radolfzell (DE); Stefan Brugger, Radolfzell (DE); Helmut Ritter, Wuppertal (DE); Christoph Weber, Constance (DE); Oliver Elsner, Allensbach (DE); Mareike Bardts, Dusseldorf (DE); Andreas Facher, Gundetswil (CH); Sven Pohle, Constance (DE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 14/255,223

(22) Filed: Apr. 17, 2014

(65) Prior Publication Data

US 2015/0297467 A1  Oct. 22, 2015

(51) Int. Cl.
*A61K 6/083* (2006.01)
*C08L 33/02* (2006.01)

(52) U.S. Cl.
CPC ............... *A61K 6/0835* (2013.01); *C08L 33/02* (2013.01)

(58) Field of Classification Search
USPC ........................................................ 523/116
See application file for complete search history.

(56) References Cited

U.S. PATENT DOCUMENTS

| | | | |
|---|---|---|---|
| 3,655,605 A | 4/1972 | Smith et al. | |
| 3,814,717 A | 6/1974 | Wilson et al. | |
| 4,035,321 A | 7/1977 | Shahidi et al. | |
| 4,089,830 A | 5/1978 | Tezuka et al. | |
| 4,143,018 A | 3/1979 | Crisp et al. | |
| 4,209,434 A | 6/1980 | Wilson et al. | |
| 4,317,681 A | 3/1982 | Beede et al. | |
| 4,360,605 A | 11/1982 | Schmitt et al. | |
| 4,374,396 A | 2/1983 | Hausdorfer | |
| 4,376,835 A | 3/1983 | Schmitt et al. | |
| 4,872,936 A | 10/1989 | Engelbrecht | |
| 5,063,257 A | 11/1991 | Akahane et al. | |
| 5,130,347 A | 7/1992 | Mitra | |
| 5,154,762 A | 10/1992 | Mitra | |
| 5,227,413 A | 7/1993 | Mitra | |
| 5,367,002 A | 11/1994 | Huang et al. | |
| 5,369,142 A | 11/1994 | Culbertson et al. | |
| 5,520,725 A | 5/1996 | Kato et al. | |
| 5,859,089 A | 1/1999 | Qian | |
| 5,962,550 A | 10/1999 | Akahane et al. | |
| 5,965,632 A | 10/1999 | Orlowski et al. | |
| 6,124,491 A | 9/2000 | Wolter et al. | |
| 7,456,232 B2 | 11/2008 | Mikulla et al. | |
| 7,649,029 B2 | 1/2010 | Kolb et al. | |
| 2005/0228113 A1 | 10/2005 | Baumer et al. | |
| 2005/0256223 A1 | 11/2005 | Kolb et al. | |
| 2005/0261393 A1 | 11/2005 | Mikulla et al. | |

FOREIGN PATENT DOCUMENTS

| | | |
|---|---|---|
| DE | 10058829 A1 | 6/2002 |
| DE | 10058830 A1 | 6/2002 |
| EP | 0323120 A2 | 7/1989 |
| EP | 0797975 A2 | 10/1997 |
| WO | 0005182 A1 | 2/2000 |
| WO | 0241845 A1 | 5/2002 |
| WO | 02062861 A1 | 8/2002 |

OTHER PUBLICATIONS

Z. Ouyang, et al; New Method . . . Reaction Glass Ionomer Cements; applied Spectroscopy 53 (1999) 297-301.
M. Marchutz, et al; European Journal of Pharmaceutical Sciences 15 (2002) 387-394.
D. Xie, et al; JMS Pure Appl. Chem., A35 (1998) 547-561.
B. M. Culbertson et al; JMS Pure Appl. Chem., A36(5&6), pp. 681-696 (1999).

*Primary Examiner* — Tae H Yoon
(74) *Attorney, Agent, or Firm* — Douglas J. Hura; Leana Levin; David A. Zdurne

(57) ABSTRACT

An aqueous dental glass ionomer composition comprising (a) a reactive particulate glass, and (b) a linear or branched polymer comprising acidic groups, which is reactive with the particulate glass in a cement reaction, whereby the linear or branched polymer comprising acidic groups has a polymer backbone and optionally pendant side chains, (c) optionally dispersed nanoparticles, and (d) optionally a low molecular compound, characterized in that the glass ionomer composition comprises—S.sub.xH groups, wherein x is an integer of from 1 to 6, which crosslink the particulate glass and/or the linear polycarboxylic acid and/or the optional dispersed nanoparticles and/or the optional low molecular compound.

13 Claims, No Drawings

DENTAL COMPOSITION

RELATED APPLICATIONS

This application is a Continuation application of U.S. patent application Ser. No. 13/388,393, filed Feb. 1, 2012, which claims the benefit from PCT Application No. PCT/EP10/01458 filed Mar. 9, 2010, which claims the priority of European Patent Application No. 09003393.7, filed on Mar. 9, 2009.

FIELD OF THE INVENTION

The present invention relates to an aqueous dental glass ionomer composition. Moreover, the present invention relates to a use of a specific polymer comprising acidic groups in an ionomer reaction with a reactive particulate glass.

BACKGROUND OF THE INVENTION

Ionomer cements are known. Conventional ionomer cements generally contain a powder component containing aluminosilicate, and a liquid portion usually containing a polymer comprising acidic groups such as polyacrylic acid, polymaleic acid, polyitaconic acid, or a copolymer of at least two of these acids, cf. "New Aspects of the Setting of Glass-ionomer Cements," Wasson et al., Journal of Dental Research; Vol. 72, No. 2, February, 1993; pages 481-483. The most common polymers comprising acidic groups are derived from polyacrylic acid or copolymers of acrylic and itaconic acid (S. Crisp), acrylic acid and maleic acid, In glass ionomer cements, the primary reactions which cause the glass ionomer cement to harden is crosslinking based on ionic forces by metal ions released from the glass of polymer comprising acidic groups. Moreover, the acids of the glass ionomer cement partially dilute metal cations from the glass structure during setting so that ionic carboxylates of metal cations may be formed during the setting process.

Dental ionomer cements are characterized by good adhesion properties to enamel and dentin, and the possibility for anticariogenic properties due to the release of fluoride from a fluoride containing glass filler. Moreover, generic cements have a number of further important advantages for applications in dentistry such as the virtual absence of an exothermic reaction, no shrinkage during setting, no free monomer in the set composition, and high dimensional stability. Accordingly, ionomer cements are widely used in the dental field for filling of a cavity, cementing of crowns, inlays, bridges, or orthodontic bands, lining of a cavity, sealing of a root canal, core construction, and preventive sealing.

However, the mechanical properties of glass ionomer cements are usually problematic since glass ionomer materials are inherently brittle. Therefore, the main limitation of the glass ionomer cements is their relative lack of strength and low resistance to abrasion and wear. Conventional glass ionomer cements have low flexural strength but high modulus of elasticity, and are therefore prone to bulk fracture. Further they exhibit rather poor optical properties.

Therefore, the restorative application of ionomer cements in posterior teeth is usually limited to non-stress bearing areas. Ionomer cement materials continue to have significant limitations for use in permanent posterior restorations, particularly with regard to large restorations.

In order to improve the mechanical properties especially flexural strength and fracture toughness, numerous investigation were carried out, such as the use of amino acid modified polymers (Z. Ouyang, S. K. Sneckberger, E. C. Kao, B. M. Culbertson, P. W. Jagodzinski, Appl. Spectros 53 (1999) 297-301; B. M. Culbertson, D. Xie, A. Thakur, J. Macromol. Sci. Pure Appl. Chem. A 36 (1999) 681-96), application of water soluble copolymers using poly(N-vinylpyrrolidone) (D. Xie, B. M. Culbertson, G. J. Wang, J. Macromol. Sci. Pure Appl. Chem. A 35 (1998) 54761), use of polyacids with narrow molecular weight distribution (DE 100 58 829) and branched polyacids (DE 100 58 830). Further polyacids having a limited molecular mass ranging from 20,000 to 50,000 Da (EP 0 797 975) and 1,000 to 50,000 Da (WO 02/41845) were proposed. A further approach was the application of spherical ionomer particles (WO 00/05182).

Resin-modified glass-ionomer cements were introduced with an aim of overcoming the problems associated with the tendency towards brittle fracture of conventional glass-ionomer, while still retaining advantages such as fluoride release and adhesion (EP 0323120, U.S. Pat. No. 4,872,936 and U.S. Pat. No. 5,154,762). Accordingly, it was suggested to replace some of the water in a conventional glass-ionomer cement with a hydrophilic monomer or to modify the polymeric acid so that some of the acid groups were replaced with polymerisable moieties, so that the polymeric acid could also take part in a polymerisation reaction.

Moreover, in order to address the problem of improving the mechanical properties of ionomer cement materials, U.S. Pat. No. 5,369,142 suggests the use of a specific acidic component, namely copolymers of acryloyl or methacryloyl derivatives of amino acids with acrylic acid or methacrylic acid. WO-A 02/062861 discloses polymer compositions for use in glass ionomer dental restoratives having improved resistance to bending and resistance to twisting, whereby the polymers are formed from at least two specific polymers. WO-A 03/061606 discloses ionomer cements containing amino acids improving the mechanical properties.

Polycondensates or heteropolycondensates based an condensable monomer compounds of silicon were described (U.S. Pat. No. 6,124,491) having a straight or branched organic chain of 4 to 50 carbon atoms and at least one double bond.

Thiolated polymers having self-crosslinking properties and their mucoadhesive properties are disclosed in Marschutz. M. K.: Bernkop-Schnurch A. European Journal of Pharmaceutical Sciences 15 (2002) 387-394.

SUMMARY OF THE INVENTION

It is the problem of the present invention to provide novel dental cement systems setting by a cement reaction whereby the cured cement has improved flexural strength and fracture toughness.

This problem is solved according to the invention by an aqueous dental glass ionomer composition comprising
(a) a reactive particulate glass, and
(b) a linear or branched polymer comprising acidic groups, which is reactive with the particulate glass in a cement reaction, whereby the linear or branched polymer comprising acidic groups has a polymer backbone and optionally pendant side chains,
(c) optionally dispersed nanoparticles, and
(d) optionally a low molecular compound, characterized in that the glass ionomer composition comprises —S$_x$H groups, wherein x is an integer of from 1 to 6, which crosslink the particulate glass and/or the linear or branched polymer comprising acidic groups and/or the optional dispersed nanoparticles and/or the optional low molecular compound.

The present invention also provides a use of a linear or branched polymer comprising acidic groups, which is reactive with a reactive particulate glass in a cement reaction, whereby the linear or branched polymer comprising acidic groups has a polymer backbone and optionally pendant side chains and comprises —$S_xH$ groups, wherein x is an integer of from 1 to 6, in a cement reaction with a reactive particulate glass.

The aqueous dental glass ionomer composition of the present invention represents a novel dental cement system setting by a cement reaction and the additional crosslinking of —$S_xH$ groups, whereby the cured cement has improved flexural strength and fracture toughness.

The crosslinking reaction may be based on an oxidative coupling of —$S_xH$ groups and/or an En-type addition of the —$S_xH$ groups to reactive double bonds and/or a Michael addition of —$S_xH$ groups to reactive alpha, beta-unsaturated moieties.

Reactive double bonds in the composition may be roughly classified in a first group of reactive double bonds which can hardly be polymerized by radical polymerization. An example of such a double bond is the allyl group. However, double bonds in this group are useful for an En-type addition of the —$S_xH$ groups to the reactive double bonds, preferably in the presence of a radical initiator. Reactive double bonds in the composition may be further roughly classified into a second group of reactive double bonds which can readily be reacted by radical polymerization. An example of such a reactive double bond is the acrylate group. Reactive double bonds in this group are useful for a Michael type addition of the —$S_xH$ groups to the reactive double bonds, preferably in the absence of a radical initiator.

The —$S_xH$ groups, wherein x is an integer of from 1 to 6, may be present on any of the reactive particulate glass, the linear or branched polymer comprising acidic groups, the optional dispersed nanoparticles, or on an optional additional low molecular compound present in the composition. Oxidative coupling of the —$S_xH$ groups, wherein x is an integer of from 1 to 6, preferably is carried out in the presence of a metal ion/oxidant system.

DETAILED DESCRIPTION OF THE PREFERRED EMBODIMENTS

The aqueous dental glass ionomer composition according to the invention comprises a reactive particulate glass. A particulate reactive glass is a powdered metal oxide or hydroxide, mineral silicate, or ion leachable glass or ceramic, that is capable of reacting with an ionomer in the presence of water to form a hydrogel. The particulate glass may contain mixed oxides of Ca, Ba, Sr, Al, Si, Zn, Na, K, B, Ag, or P. Examples of particulate reactive glass materials include materials commonly known in the art of glass-ionomer cements such as calcium or strontium-containing and aluminum-containing materials. Preferably, particulate reactive fillers contain leachable fluoride ions.

Specific examples of particulate reactive glasses are selected from calcium aluminosilicate glass, calcium aluminumfluorosilicate glass, calcium aluminumfluoroborosilicate glass, strontium aluminosilicate glass, strontium aluminofluorosilicate glass, strontium aluminofluoroborosilicate glass. Suitable particulate reactive glasses further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835. In a preferred embodiment, the particulate glass is a barium and/or strontium fluoroalumosilicate glass.

The particulate reactive glass may be surface modified by a surface modifying agent. The surface modifying agent contains a modifying compound providing a dual function. The modifying compound is capable of reacting with surface atoms of the particulate reactive glass, thereby forming a covalent bond between the surface atoms of the particulate reactive and the modifying compound.

Moreover, the modifying compound may contains one or more capable of taking part in a crosslinking reaction, thereby facilitating the additional crosslinking, whereby the cured cement has improved flexural strength and fracture toughness. The modifying agent may contain one or more modifying compounds.

Preferably, the surface modifying agent contains a hydrolyzable organofunctional silicon compound. The hydrolyzable organofunctional silicon compound may be a compound of one of the following formulae (I), (II) and (III), or a hydrolysis product thereof.

$X_m R_{3-m} SiL$ (I)
$X_m R_{2-m} SiL'L''$ (II)
$X_m SiUL'L'''$ (III)

wherein
X represents a hydrolyzable group;
R represents an alkyl, cycloalkyl, cycloalkylalkyl, aralkyl or aryl group,
L, L', L", and L''' which may be the same or different represent independent from each other an organic group containing one or more —$S_xH$ groups, wherein x is an integer of from 1 to 6;
m is an integer
whereby the sum of X, R, L, L', L", and L''' is 4 for each of formula (I), (II), and (III).

Preferably, X is a halogen atom or $OR^1$, wherein $R^1$ is an alkyl, cycloalkyl, cycloalkylalkyl, aralkyl or aryl group. More preferably, R or $R^1$ are independently an alkyl group.

In order to impart crosslinking capability to the organofunctional silicon compound, L, L', L", and L''' contain —$S_xH$ groups, wherein n is an integer of from 1 to 6. In a preferred embodiment, L, L', L", and L''' may be represented by the following formula:

$$—[(CH_2)_o Z]_q (C_2)_p S_x H$$

wherein the Z which may be the same or different and are independent from each other, represent —NR'—, —O—, S or PR', wherein R' represents independently a hydrogen atom, an alkyl group, a cycloalkyl group, an cycloalkylalkyl group, an aralkyl group or an aryl group, o and p, which are independent from each other, may be the same or different and represent an integer of from 1 to 6, q represents an integer of from 0 to 12, and x is an integer of from 1 to 6, In a further preferred embodiment, L, L', L", and L''' may be represented by the following formula:

$$—[(CH_2)_o NR']_q (CH_2)_p S_x H$$

wherein R', which are independent from each other, may be the same or different and represent a hydrogen atom, an alkyl group, a cycloalkyl group, an cycloalkylalkyl group, an aralkyl group or an aryl group, o and p, which are independent from each other, may be the same or different and represent an integer of from 1 to 6, q represents an integer of from 0 to 12 and x is an integer of from 1 to 6.

In a still further preferred embodiment, L, L', L", and L''' may be represented by the following formula:

$$—[(CH_2)_o Z]_q (CH_2)_p S_x H$$

wherein Z represents an oxygen atom or a sulfur atom, o and p, which are independent from each other, may be the same or different and represent an integer of from 1 to 6, q represents an integer of from 0 to 12, and x is an integer of from 1 to 6.

An alkyl group may be straight-chain or branched $C_{1\text{-}16}$ alkyl group, typically a $C_{1\text{-}8}$ alkyl group. Examples for a $C_{1\text{-}6}$ alkyl group can include linear or branched alkyl groups having 1 to 6 carbon atoms, preferably 1 to 4 carbon atoms, for example, methyl, ethyl, n-propyl isopropyl, n-butyl, isobutyl, sec-butyl, tert-butyl, n-pentyl, isopentyl and n-hexyl. A cycloalkyl group may be a $C_{3\text{-}16}$ cycloalkyl group. Examples of the cycloalkyl group can include those having 3 to 14 carbon atoms, for example, cyclopropyl, cyclobutyl, cyclopentyl and cyclohexyl. A cycloalkylalkyl group can include those having 4 to 22 carbon atoms. Examples for a cycloalkylalkyl group can include a combination of a linear or branched alkyl group having 1 to 6 carbon atoms and a cycloalkyl group having 3 to 14 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, propylcyclopentyl, propylcyclohexyl. An aralkyl group may be a $C_{7\text{-}26}$ aralkyl group, typically a combination of a linear or branched alkyl group having 1 to 6 carbon atoms and an aryl group having 6 to 10 carbon atoms. Specific examples of an aralkyl group are a benzyl group or a phenylethyl group. An aryl group can include aryl groups having 6 to 10 carbon atoms. Examples of the aryl group are phenyl and naphtyl.

The $C_{1\text{-}8}$ alkyl group and the $C_{3\text{-}14}$ cycloalkyl group may optionally be substituted by one or more members of the group selected from a $C_{1\text{-}4}$ alkyl group, $C_{1\text{-}4}$ alkoxy group, a phenyl group, and a hydroxy group. Examples for a $C_{1\text{-}4}$ alkyl group can include linear or branched alkyl groups having 1 to 4 carbon atoms, for example, methyl, ethyl, n-propyl, isopropyl, n-butyl, isobutyl, sec-butyl, tent-butyl. Examples for an $C_{1\text{-}4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Aryl groups may contain 1 to 3 substituents. Examples of such substituents can include halogen atoms, $C_{1\text{-}4}$ alkyl groups, $C_{1\text{-}4}$ alkoxy groups, $C_{1\text{-}4}$ alkylthio groups, $C_{1\text{-}4}$ alkylsulfonyl groups, carboxyl group, $C_{2\text{-}6}$ alkoxycarbonyl groups, and $C_{1\text{-}4}$ alkylamino groups. Here, illustrative of the halogen atoms can be fluorine, chlorine, bromine and iodine. The $C_{1\text{-}4}$ alkyl groups are, for example, methyl, ethyl, n-propyl, isopropyl and n-butyl. Illustrative of the $C_{1\text{-}4}$ alkoxy groups are, for example, methoxy, ethoxy and propoxy. Illustrative of the $C_{1\text{-}4}$ alkylthio groups are, for example, methylthio, ethylthio, and propylthio. Illustrative of the $C_{1\text{-}4}$ alkysulfonyl groups are, for example, methylsulfonyl, ethylsulfonyl and propylsulfonyl. Illustrative of the $C_{2\text{-}5}$ alkoxycarbonyl groups can be those having alkoxy groups each of which contains 1 to 4 carbon atoms, for example, methoxycarbonyl, ethoxy carbonyl and propoxycarbonyl. Illustrative of the $C_{1\text{-}8}$ alkylamino groups can be those having one or two alkyl groups each of which contains 1 to 4 carbon atoms, for example, methylamino, dimethylamino, ethyl amino and propylamino. The alkyl moieties in these substituents may be linear, branched or cyclic.

Specific examples of modifying compounds contained in the surface modifying agent used in the present invention are 3-mercaptopropyltrimethoxysilane, 3-mercaptopropyltriethyldimethoxysilane, 3-mercaptopropyldimethylmethoxysilane, 3-mercaptopropyltriethoxysilane, 3-mercaptopropylmethyldiethoxysilane, 3-mercaptopropyldimethylethoxysilane. The compounds may be used alone or in combination of two or more different compounds.

Based on the treatment of the particulate reactive glass with the surface active agent, the surface of the reactive filler displays —$S_xH$ groups, wherein x is an integer of from 1 to 6. The —$S_xH$ groups, wherein x is an integer of from 1 to 6, correspond for example to the groups L, L', L", and L"' as described above.

The surface modifying agent may be used as such or dissolved or dispersed in a suitable solvent. Examples of suitable solvent are toluene, methanol, ethanol, isopropanol, and ethylacetate.

The particulate reactive glass usually has an average particle size of from 0.005 to 100 .mu.m, preferably of from 0.01 to 40 .mu.m as measured using, for example, by electron microscopy or by using a conventional laser diffraction particle sizing method as embodied by a MALVERN Mastersizer S or MALVERN Mastersizer 2000 apparatus. The particulate reactive glass may be a multimodal particulate reactive glass representing a mixture of two or more particulate fractions having different average particle sizes. The particulate reactive glass may also be a mixture of particles of different chemical composition. In particular, it is possible to use a mixture of a particulate reactive material and a particulate non-reactive material.

The aqueous dental glass ionomer composition according to the invention preferably comprises 40 to 80 percent by weight, more preferably 45 to 70 percent by weight, of the reactive particulate glass, based on the weight of the entire composition.

The aqueous dental glass ionomer composition according to the invention further comprises a linear or branched polymer comprising acidic groups, which is reactive with the particulate glass in a cement reaction.

The linear or branched polymer comprising acidic groups preferably contains pendant groups containing one or more groups selected from acidic groups, carbon-carbon double bonds, alpha,beta unsaturated moieties, and —$S_xH$ groups, wherein x is an integer of from 1 to 6, preferably from 1 to 3, more preferably 1 or 2. In a preferred embodiment, the linear or branched polymer comprising acidic groups has pendant thiol groups.

The linear or branched polymer comprising acidic groups has a polymer backbone and optionally pendant side chains. The polymer backbone is obtainable by a process comprising the step of polymerizing a mixture containing one or more monomers. The monomers may include acrylic acid, itaconic acid, methacrylic acid and esters or anhydrides thereof. The pendent acidic groups of the polymer comprising acidic groups must be sufficient in number or percent by weight to bring about the setting or curing reaction in the presence of the particulate reactive glass. The acidic groups may be selected from carboxylic acid groups, phosphoric acid groups, phosphonic acid groups, and sulfonic acid groups. Among these acidic groups, carboxylic acid groups are preferred.

The linear or branched polymer comprising acidic groups may optionally contain pendant side chains. The pendant side chains may comprise —$S_xH$ groups, wherein x is an integer of from 1 to 6. The —$S_xH$ group containing side chains may be introduced to the polymer backbone by reacting a portion of the acidic groups, in particular carboxylic groups, with a bi-functional compound. Examples of suitable bi-functional monomers may be aminothiols, specifically the following compounds may be mentioned.

By adding a resin component containing —S.sub.xH groups, wherein x is an integer of from 1 to 6, to the ionomer cement, not only the brittleness may be further improved, but also the mechanical strengths and physical properties such as adhesiveness to a tooth structure are improved.

It is possible to create a source of additional covalent cross-linking, which imparts additional strength to the ultimate ionomeric cement composition, by reacting a portion of the carboxylic acid groups with a further bifunctional monomer containing a carbon-carbon double bond which can take part in an ene-type reaction with the —S.sub.xH groups present in the composition, and/or with a bifunctional monomer containing a reactive alpha,beta-unsaturated moiety which can take part in Michael addition reaction with the —S.sub.xH groups present in the composition, and optionally in a radical polymerization reaction.

Examples of suitable bifunctional monomers include acryloyl chloride, methacryloyl chloride, vinyl azalactone, allyl isocyanate, 2-hydroxyethylmethacrylate (HEMA), 2-aminoethylmethacrylate, 2-isocyanatoethyl methacrylate (IEM), acrylic acid, methacrylic acid and N-vinylpyrrolidone. Other examples of suitable bi-functional monomers are described in U.S. Pat. No. 4,035,321 U.S. Pat. No. 5,130,347.

The linear or branched polymer comprising acidic groups preferably has a molecular weight Mw in the range of from 1,000 to 200,000, more preferably 5,000 to 180,000.

The aqueous dental glass ionomer composition according to the invention preferably comprises 10 to 60 percent by weight, more preferably 15 to 55 percent by weight, of the linear or branched polymer containing acidic groups, based on the weight of the entire composition.

The aqueous dental glass ionomer composition according to the invention optionally comprises dispersed nanoparticles. The nanoparticles may be nanocondensates obtainable by condensing a mixture containing one or more compounds formula (I), (II), or (III) as defined above. The condensation of the silane may be carried out by acid catalysis. Suitable acids may be selected from mineral acids such as hydrofluoric acid, hydrochloric acid, phosphoric acid, and sulfuric acid. Condensation may be carried out in the presence of further hydrolysable metal compounds such as metal alkoxides selected from alkoxides of titanium, zirconium, cerium, ytterbium, aluminum, tin, and yttrium. In the absence of co-condensable metal compounds, the particle size distribution is usually narrower than in case of the presence of co-condensable metal compounds. In a preferred embodiment, the dispersed nanoparticles of the aqueous dental glass ionomer composition according to the invention have pendant thiol groups.

The aqueous dental glass ionomer composition according to the invention may comprise from 0 to 75 percent by weight of dispersed nanoparticles based on the weight of the entire composition. Preferably, the composition contains 5 to 50 percent by weight of dispersed nanoparticles based on the weight of the entire composition. In a preferred embodiment, the dispersed nanoparticles have an average particle size of from 1 to 100 nm.

The glass ionomer composition of the present invention may optionally further contain a low molecular compound. The low molecular compound may have a molecular weight Mw in the range of from 100 to 5000, preferably in the range of from 200 to 2000. The low molecular compound may contain one or more —S.sub.x1-1 groups, wherein x is an integer of from 1 to 6. Alternatively, the low molecular compound may contain moieties which may react with the —S.sub.xH groups present in the glass ionomer composition in an ene-type reaction or a Michael addition reaction. Specific examples for suitable polythiol compounds are PEG dithiol (e.g. Aldrich 704369, average molecular weight: 1,500; Aldrich704539 average molecular weight: 3,400), 1,16-Hexadecanedithiol, peptides such as Asn-Arg-Cys-Ser-Gln-Gly-Ser-Cys-Trp-Asn, Reduced=85% (HPLC) C44H67N17O16S2, 1154.24, Trithiocyanuric acid, tetrathiol- and tetrapyrrole-substituted Tetrathiafulvalene derivatives, pentaerythrityl tetrathiol, trimethylolpropane tris (2-mercaptoacetate), trimethylolpropane tris(3-mercaptopropionate), 2,2'-(ethylenedioxy)diethanethiol and pentaerythrital tetrakis(3-mercaptopropionate). Moreover, suitable polythiol compounds may also be selected from the following compounds:

Moreover, suitable compounds may also be selected from the following polyene compounds: trimethylol propane triallyl ether 2,4,6-triallyloxy-1,3,5-triazine or triallyl-1,3,4-triazine-2,4,6-(1H, 3H, 5H)-trione.

The glass ionomer composition of the present invention is characterized in that the glass ionomer composition comprises —S.sub.x H groups, wherein x is an integer of from 1 to 6, which crosslink the particulate glass and/or the linear polymer comprising acidic groups and/or the optionally dispersed nanoparticles and/or the low molecular compound.

The —S.sub.x H groups, wherein x is an integer of from 1 to 6, are sulfane or polysulfane groups, wherein x is preferably 1 to 3. Specifically, the —S.sub.x H groups are preferably thiol groups (—SH), disulfane groups (—S—SH) or trisulfane groups (—S—S—SH). In a more preferred embodiment —S.sub.xH groups are thiol groups which may be primary or secondary thiol groups.

When the crosslinking reaction is based on an oxidative coupling of —S.sub.xH groups, the —S.sub.xH groups, wherein x is an integer of from 1 to 6, may be present on any of the reactive particulate glass, the linear or branched polymer containing acidic groups, the optional dispersed nanoparticles, or on the optional low molecular compound present in the composition. Preferably, oxidative coupling is metal catalyzed oxidative coupling in the presence of an oxidizing agent. Accordingly, the composition contains preferably a transition metal ions and an oxidizing agent. Examples of the transition metal ions are iron and manganese ions. Moreover, the composition preferably contains an oxidizing agent. Examples for a suitable oxidizing reagent are peroxides such as hydrogen peroxide or a peroxide compound commonly used as free-radical polymerization initiators.

In a first preferred embodiment, the —S.sub.xH groups are present exclusively on either the reactive particulate glass, the linear or branched polymer containing acidic groups, or the optional dispersed nanoparticles. In case the —S.sub.xH groups are present exclusively on an optional additional low molecular component present in the composition, then it will be necessary that the reactive particulate glass, the linear or branched polymer containing acidic groups, and/or the optional dispersed nanoparticles contain reactive carbon-carbon double bonds which may take part in an ene-type reaction or a Michael addition with the —S.sub.xH groups. Specifically, the —S.sub.xH groups may be present on the linear or branched polymer containing acidic groups.

In a second preferred embodiment, the —S.sub.xH groups are present on at least two members selected from the group of either the reactive particulate glass, the linear or branched polymer containing acidic groups, the optional dispersed nanoparticles, or the optional low molecular compound. Any other member selected from this group may contain reactive carbon-carbon double bonds which may take part in an ene-type reaction or the Michael addition with the —S.sub.xH groups.

In a third preferred embodiment each of the members selected from the group of the reactive particulate glass, the linear or branched polymer containing acidic groups, the optional dispersed nanoparticles, or the optional low molecular compound contains either —S.sub.xH groups or reactive carbon-carbon double bonds which may take part in an ene-type reaction with the —S.sub.xH groups.

Accordingly, in the aqueous dental glass ionomer composition according to the invention, the —S.sub.xH groups may crosslink the particulate glass and/or the linear or branched polymer containing acidic groups and/or the optionally dispersed nanoparticles by oxidative coupling.

In a further preferred embodiment, the sulfane or polysulfane groups of the aqueous dental glass ionomer composition according to the invention crosslink the particulate glass and/or the linear polymer containing acidic groups and/or the optionally dispersed nanoparticles in the absence of oxygen. Preferably, the —S.sub.xH groups in the aqueous dental glass ionomer composition according to the invention crosslink by an —S.sub.xH ene-reaction or a Michael addition.

The dental glass ionomer compositions of the present invention may further contain catalysts for the cross-linking reaction, free-radical polymerization initiators, stabilizers, non-reactive fillers, solvents, pigments, nonvitreous fillers, free radical scavengers, polymerization inhibitors, reactive and nonreactive diluents, coupling agents to enhance reactivity of fillers, rheology modifiers, and surfactants (such as to enhance solubility of an inhibitor e.g., polyoxyethylene).

Suitable catalysts for the cross-linking reaction may comprise metal cations, metal complexes and/or metal particles such as metal powder or metal colloids, either alone or in combination with an oxidizing agent such as oxygen, a peroxide and/or an oxidizing metal complex. In one aspect, the catalyst and oxidizing agent may comprise the same material. The metal cations, metal complexes and/or metal particles may comprise iron, nickel, copper, cobalt or platinum atoms, or the corresponding ions thereof The peroxide may comprise hydrogen peroxide, urea-hydrogen peroxide, ethylmethylketone peroxide, or benzoylperoxide.

Suitable free-radical polymerization initiators may be selected from organic peroxides such as benzoylperoxide, methylethylketone peroxide, acetone peroxide and tert-butyl hydroperoxide, azo compounds such as azobisisobutyronitrile and 1,1'azobis(cyclohexanecarbonitrile), and halogens such as chlorine, bromine or iodine.

Suitable stabilizers may be selected from reducing agents such as vitamin C, inorganic sulfides and polysulfides and the like.

Suitable non-reactive fillers may be selected from fillers currently used in dental restorative compositions. The filler should be finely divided and preferably has a maximum particle diameter less than about 100 .mu.m and an average particle diameter less than about 10 .mu.m. The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque. Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

Suitable solvents or nonreactive diluents include alcohols such as ethanol and propanol. Suitable reactive diluents are alpha,beta unsaturated monomers for providing altered properties such as toughness, adhesion, and set time, e.g., 2-hydroxyethyl methacrylate (HEMA), hydroxypropyl methacrylate.

Suitable alpha,beta-unsaturated monomers may be water-soluble, water-miscible or water-dispersible. Water-soluble, water-miscible or water-dispersible acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcycelohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methaeryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methaeryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methaeryloxyethyl-4-cyclohexyl carbamate, 2,2'-bis(4-methacryloxyphenyl)propane, 2,2'bis(4-acryloxyphenyl)propane, 2,2'-bis[4 (2-hydroxy-3-methacryloxy-phenyl)]propane, 2,2'-bis[4(2-hydroxy-3-acryloxy-phenyl)propane, 2,2'-bis(4-methacnyloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyepropane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methaerylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Mixtures of alpha,beta-unsaturated monomers can be added if desired. Preferably, the mixed but unset cements of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset cement components.

An example of a suitable free radical scavenger is 4-methoxyphenol.

Suitable polymerization inhibitors may be selected from hydroxytoluene, butylated hydroxytoluene (BHT), hydroquinone, 1,4-benzoquinone: tert-butylpyrocatechol, toluhydroquinone, and 3,4-di-tert-butyl-p-cresol. The amount of inhibitor may be selected from 0.001 to 2% and preferably from 0.02 to 0.5% based on the total weight of the copolymer/comonomer/water mixture.

External energy may alternatively or additionally be employed in order to crosslink the —$S_{xH}$ groups by oxidative coupling. Sources of external energy may be selected from radiative energy sources such as thermal energy sources, ultrasound energy sources, and/or light energy sources such as ultraviolet lamps or visible lamps. In the event that light energy is employed to crosslink the —$S_{xH}$ groups by oxidative coupling, the dental glass ionomer composition may additionally comprise photoinitiators and/or photosensitizers such as molecular oxygen, alpha-diketones, orthoquinones, organic dyes, fluorescent dyes or colorants, and/or azo-compounds such as azobisisobutyronitrile and 1,1'azobis(cyclohexanecarbonitrile).

The dental glass ionomer composition may be used in a dental ionomer cement. Two major classes of such cements may be distinguished. The first class relates to conventional glass ionomers employing as their main ingredients a homopolymer or copolymer of an alpha,beta-unsaturated carboxylic acid (e.g., poly acrylic acid, copoly (acrylic, itaconic acid), etc.), a modified particulate reactive filler such as modified fluoroaluminosilicate glass, water, and a chelating agent such as tartaric acid. Such dental ionomer cements may be supplied in powder/liquid formulations that are mixed just before use. The mixture will undergo self-hardening in the dark due to an ionic reaction between the acidic groups of the polycarboxylic acid and cations leached from the glass as well as the crosslinking reaction based on the —$S_{xH}$ groups. The second major class relates to resin-modified glass ionomer cements. Like a conventional glass ionomer, a resin-modified glass ionomer cement employs a modified particulate reactive filler obtainable according to the process of the present invention, whereby the organic portion of an resin-modified glass ionomer cements is different. In one type of resin-modified glass ionomer cement, the polycarboxylic acid is modified to replace or end-cap some of acidic repeating units with pendent curable groups and a photoinitiator is added to provide a second cure mechanism, e.g., as in U.S. Pat. No. 5,130,347. Acrylate or methacrylate groups may be employed as the pendant curable group. A redox cure system can be added to provide a third cure mechanism, e.g., as in U.S. Pat. No. 5,154,762. In another type of resin-modified glass ionomer cement, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257, U.S. Pat. No. 5,520,725, U.S. Pat. No. 5,859,089 and U.S. Pat. No. 5,962,550. Various monomer-containing or resin-containing cements are also shown in U.S. Pat. No. 4,872,936, U.S. Pat. No. 5,227,413, U.S. Pat. No. 5,367,002 and U.S. Pat. No. 5,965,632. Resin-modified glass ionomer cements may be formulated as powder/liquid or paste/paste systems, and contain water as mixed and applied. They harden in the dark due to the ionic reaction between the acidic groups of the polycarboxylic acid and cations leached from the glass as well as the crosslinking reaction of the particulate glass and/or the linear polycarboxylic acid and/or the optionally dispersed nanoparticles when the pH of the aqueous dental glass ionomer composition is at least 6 at the end of the main setting reaction of the linear polycarboxylic acid reactive with the particulate glass. Moreover, resin-modified glass ionomer cements also cure on exposure of the cement to light from a dental curing lamp.

Methods for preparing the glass ionomer compositions are well known. (Crisp et al., "Glass ionomer cement formulations. II. The synthesis of novel polycarboxylic acids,"in J. Dent. Res. 59 (6): 1055-1063 (1980)). A dental ionomer cement is prepared by mixing the ionomer with the particulate reactive filler and optionally nanoparticles in the presence of water. The components of the ionomer cement system can be combined (such as by mixing or blending) in a variety of manners and amounts in order to form the ionomer cements of the present invention. For example, a concentrated aqueous solution of the ionomer may be mixed with the modified particulate reactive filler and optionally further components at the time of use. The resultant combination of ionomer, modified particulate reactive filler and water allows the setting reaction to begin. Alternatively, the ionomer and the modified particulate reactive filler are provided as a freeze-dried or lyophilized powdered blend under conditions in which there is not sufficient water to allow the setting reaction to proceed. Such systems can then be combined with water at the time of use in order to begin the setting reaction. Once the setting reaction has begun, the resultant mixture may be formed into its desired shape, followed by curing and allowing the mixture to fully harden. In general, the weight-to-weight ratio of the ionomer to water is from about 1:10 to about 10:1. In general, the concentration of ionomer in water ranges from 25 to 90% by weight, and preferably from 40 to 65% by weight. The resultant aqueous solution has a ratio of polymer to liquid generally ranging from about 1.5 to 8.

The reaction mixture may also include a modifying agent such as tartaric acid, for adjusting the working time and a setting time, respectively, when preparing the cement as described in U.S. Pat. No. 4,089,830, U.S. Pat. No. 4,209,434, U.S. Pat. No, 4,317,681 and U.S. Pat. No. 4,374,936. In general, an increase in working time results in an increase in setting time as well. The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application. The "setting time" is the time measured from the beginning of the setting reaction in a restoration to the time sufficient hardening has occurred to allow subsequent clinical or surgical procedures to be performed on the surface of the restoration.

In the setting reaction, the modified particulate reactive glass behaves like a base and reacts with the acidic ionomer to form a metal polysalt which acts as the binding matrix (Prosser, J. Chem. Tech. Biotechnol. 29:69-87 (1979)). Moreover, due to the presence of —$S_xH$ groups, crosslinking of the particulate glass and/or the linear polycarboxylic acid and/or the optionally dispersed nanoparticles when the pH of the aqueous dental glass ionomer composition is at least 6 during the reaction of the linear polycarboxylic acid reactive with the particulate glass takes place. Thereby the bonding within the cement does not only rely on ionic salt bridges which are problematic with regard to the mechanical properties, but also on covalent and complex bonding. The setting reaction is therefore characterized as a dual chemical cure system that proceeds automatically in the presence of water. The cement sets to a gel-like state within a few minutes and rapidly hardens to develop strength. Further reactions are polymerisation reactions and polyaddition reactions.

The dental composition is a multi-pack, preferably a two-pack composition. The composition may be a paste/paste system, a powder/liquid system, or a liquid/paste system. The composition is designed so as to avoid premature curing of the components. For this purpose, the reactive inorganic filler component and any acid group containing component must be formulated so as to avoid a premature cement reaction. In a first embodiment, the reactive inorganic glass is contained in a first pack and any acid group containing component is contained in a second pack. The first pack may be a powder or a paste. The second pack may be a liquid or paste. In a second embodiment, the first pack is a powder comprising the reactive inorganic filler and a solid polyacid such as polyacrylic acid, and the second pack is a paste or liquid and contains a further acid group containing component.

The ratio of powder to liquid affects the workability of the mixed ionomer cement systems. Weight ratios higher than 20:1 tend to exhibit poor workability, while ratios below 1:1 tend to exhibit poor mechanical properties, e.g., strength, and hence are not preferred. Preferred ratios are on the order of about 1:3 to about 6:1 and preferably about 1:1 to 4:1

The invention will now be further illustrated by the following Examples. All percentages refer to percentages by weight unless stated otherwise.

EXAMPLES

Preparation Example 1 and 2

General procedure for polymer analogous reaction of polyacrylic acid (PAA) with aminoalkylthiols according to M. K. Marschutz, A. Bernkop-Schurch, Europ. J. Pharm. Sci. 15 (2002) 387-394.

PAA was hydrated in demineralised water and the pH value of the PAA solution was adjusted to 6 by addition of aqueous sodium hydroxide. Then, 1-ethyl-3-(3-dimethylaminopropyl) carbodiimide hydrochloride (EDAC, Sigma Aldrich) was added. After 20 minutes stirring at room temperature, the aminoalkylthiol was added and the pH was readjusted to 6. Then reaction mixture was reacted for 24 h at room temperature under stirring. The resulting reaction product was isolated by dialysis. Precipitated polymer was dissolved in concentrated sodium hydroxide solution, neutralized and then dialyzed.

| Substance | Preparation Example 1 | | Preparation Example 2 | |
|---|---|---|---|---|
| | g | mmol | g | mmol |
| PAA, M 135000 | 0.5 | 6.9 | 0.5 | 6.9 |
| Cysteamine HCl | 0.91 | 8 | 0.91 | 8 |
| EDAC | 2.3 | 12 | 1.53 | 8 |
| Conversion | 35-52% | | 44-55% (cysteamine) | |

The conversion of cysteamine was determined by elementary analysis of nitrogen:

| | Preparation Example 1 | Preparation Example 2 |
|---|---|---|
| % C | 38.99 | 37.43 |
| % H | 5.99 | 7.39 |
| % N | 5.53 | 5.85 |

Preparation Example 3 to 5

General procedure for polymer analogous reaction of polyacrylic acid (PAA) with allyl amine PAA was dissolved in 15 ml DMF at 60.degree. C. and allyl amine was added. Dicyclohexylcarbodiimide was solved in 1 ml DMF and added to the polymer solution. The solution was stirred 24 hours at 60.degree. C. The solution was concentrated under vacuum and the polymer was precipitated in ethyl acetate. The conversion of allyl amine was determined by 1H-NMR spectroscopy:

$^1$H-NMR [ppm]: $\delta$(600 MHz, DMSO-$D_6$) =1.32-1.9 ($CH_2$); 2.1-2.5 (CH); 5-5.2 ($CH_2\text{=}CH$); 7.99 (1OH)

| Substance | Preparation Example 3 | | Preparation Example 4 | | Preparation Example 5 | |
|---|---|---|---|---|---|---|
| | g | mmol | g | mmol | g | mmol |
| PAA, M 136000 | 0.5 | 6.9 | 0.5 | 6.9 | 0.5 | 6.9 |
| Allyl amine | 0.03 | 0.48 | 0.05 | 0.83 | 0.09 | 1.52 |
| Dicyclohexylcarbodiimide | 0.11 | 0.51 | 0.18 | 0.86 | 0.34 | 1.65 |
| Conversion (allyl amine) | 4.3% | | 5% | | 7.7% | |

Preparation Example 6

In the same manner as in Preparation examples 3 to 5, PAA was dissolved in 15 ml DMF at 60.degree. C. and allyl amine was added in order to attain a conversion rate of 19%. Dicyclohexylcarbodiimide was dissolved in 1 ml DMF and added to the polymer solution.

The solution was stirred 24 hours at 60.degree. C. The solution was concentrated under vacuum and the polymer was precipitated in ethyl acetate. The conversion of allyl amine was confirmed by $^1$H-NMR spectroscopy to be 12% (allyl amine).

Application Example 2.4 g of the aminoalkylthiol modified polyacid of Preparation example 1 and 0.39 g tartaric acid were dissolved in 3.21 mL demineralized water (liquid 1).

A 30 wt % aqueous solution of the allyl amine modified polyacid of Preparation example 6 containing 7.9 wt % camphorquinone and 5.25 wt % N,N-dimethylethylenediamine (liquid 2) was prepared.

Liquid 1 and liquid 2 were mixed manually in a ratio of 6:4.

In a subsequent step this mixture was mixed manually with the powder, a strontium-sodium-phosphor-aluminium-fluorosilicate glass, in a ratio of 2:1.

Biaxial flexural strength was determined using disk shaped specimens of 20 mm diameter and 1 mm thickness.

The preparation of the specimens was performed under yellow light conditions.

The specimens were irradiated for 60 s each site in a Licu-Lite irradiation oven, and stored for 1 h at 37.degree. C., 95% relative humidity, and subsequently for 23.+−.0.5 h in demineralized water at 37.degree. C.

As a reference example non-irradiated specimens were used.

All tests were performed on a Zwick Z020 universal testing machine.

TABLE-US-00004 Irradiated sample Non-irradiated sample Biaxial flexural 27.3 .+−. 2.4 20.8.+−. 4.0 strength [MPa]

What is claimed:

1. An aqueous dental glass ionomer composition comprising (a) a reactive particulate glass, and (b) a linear or branched polymer comprising acidic groups, which is reactive with the particulate glass in a cement reaction, whereby the linear or branched polymer comprising acidic groups has a polymer backbone and optionally pendant side chains, (c) optionally dispersed nanoparticles, and (d) optionally a low molecular compound, characterized in that the glass ionomer composition comprises —$S_xH$ groups, wherein x is an integer of from 1 to 6, which crosslink the particulate glass and/or the linear or branched polymer comprising acidic groups and/or the optional dispersed nanoparticles and/or the optional low molecular compound.

2. The aqueous dental glass ionomer composition according to claim 1, wherein the —$S_xH$ groups crosslink by metal catalyzed oxidative coupling in the presence of an oxidizing agent.

3. The aqueous dental glass ionomer composition according to claim 1, wherein —$S_xH$ groups crosslink by an —SH ene-reaction of the —$S_xH$ groups to reactive double bonds of an allyl group in the presence of a radical initiator.

4. The aqueous dental glass ionomer composition according to claim 1, wherein —$S_xH$ groups crosslink by a Michael addition.

5. The aqueous dental glass ionomer composition according to claim 1, wherein the —$S_xH$ groups comprise thiol groups.

6. The aqueous dental glass ionomer composition according to claim 5, wherein the thiol groups are primary thiol groups.

7. The aqueous dental glass ionomer composition according to claim 1, wherein the linear or branched polymer comprising acidic groups has pendant groups containing one or more groups selected from acidic groups, carbon-carbon double bonds and —$S_xH$ groups, wherein x is an integer of from 1 to 6.

8. The aqueous dental glass ionomer composition according to claim 1, wherein the linear polymer comprising acidic groups has pendant thiol groups.

9. The aqueous dental glass ionomer composition according to claim 1, wherein the dispersed nanoparticles have pendant thiol groups.

10. The aqueous dental glass ionomer composition according to claim 1, comprising 40 to 80 percent by weight of the reactive particulate glass, based on the weight of the entire composition and/or comprising 10 to 60 percent by weight of the polymer comprising acidic groups, based on the weight of the entire composition, and/or comprising up to 75 percent by weight of dispersed nanoparticles based on the weight of the entire composition.

11. The aqueous dental glass ionomer composition according to claim 1, wherein the particulate glass contains mixed oxides of Ca, Ba, Sr, Al, Si, Zn, Na, K, B, Ag, or P, or wherein the particulate glass contains fluoride.

12. The aqueous dental glass ionomer composition according to claim 1 which is a two component composition.

13. The aqueous dental glass ionomer composition according to claim 1, wherein the linear or branched polymer comprising acidic groups, comprises —$S_xH$ groups, wherein x is an integer of from 1 to 6.

* * * * *